United States Patent [19]
Pfeil et al.

[11] Patent Number: 5,237,385
[45] Date of Patent: Aug. 17, 1993

[54] SAMPLE PROCESSING

[75] Inventors: David L. Pfeil, Winthrop; Robert W. Foster, Foxboro; Carrol J. Hoffman, Westwood, all of Mass.

[73] Assignee: Thermo Jarrell Ash Corporation, Waltham, Mass.

[21] Appl. No.: 761,494

[22] Filed: Sep. 18, 1991

[51] Int. Cl.$^5$ .................... G01N 1/14; G01N 35/00; G01N 21/73
[52] U.S. Cl. .................... 356/311; 356/316; 73/864.81
[58] Field of Search ............... 356/311, 315, 316, 417, 356/36; 73/864.81, 864.83, 864.84, 864.85; 422/81; 436/52

[56] References Cited

U.S. PATENT DOCUMENTS

| | | | |
|---|---|---|---|
| 4,528,158 | 7/1985 | Gilles | 422/63 |
| 4,590,165 | 5/1986 | Gilles | 436/49 |
| 4,684,251 | 8/1987 | Brouwer et al. | 356/315 |
| 4,794,806 | 1/1989 | Nicoli et al. | 73/864.85 |
| 4,804,519 | 2/1989 | Sainz | 422/81 |

*Primary Examiner*—F. L. Evans
*Attorney, Agent, or Firm*—Fish & Richardson

[57] ABSTRACT

A sample processing system for use with analysis apparatus includes tubular structure that defines a continuous elongated flow chamber. The tubular structure has an inlet port at one end, an outlet port at the other end, and a sample inlet port in communication with the continuous elongated flow chamber between the inlet and outlet ports. A first pump flows diluent at a first rate through the inlet port for flow through the continuous elongated flow chamber, and a second pump flows a liquid mixture from the continuous elongated flow chamber through the outlet port at a rate greater than the first rate. With the sample inlet port submerged in a sample to be analyzed, the sample is aspirated through the sample inlet port into the flowing diluent stream in the continuous elongated flow chamber for dilution and application of the diluted sample mixture to sample analysis apparatus for analysis.

17 Claims, 1 Drawing Sheet

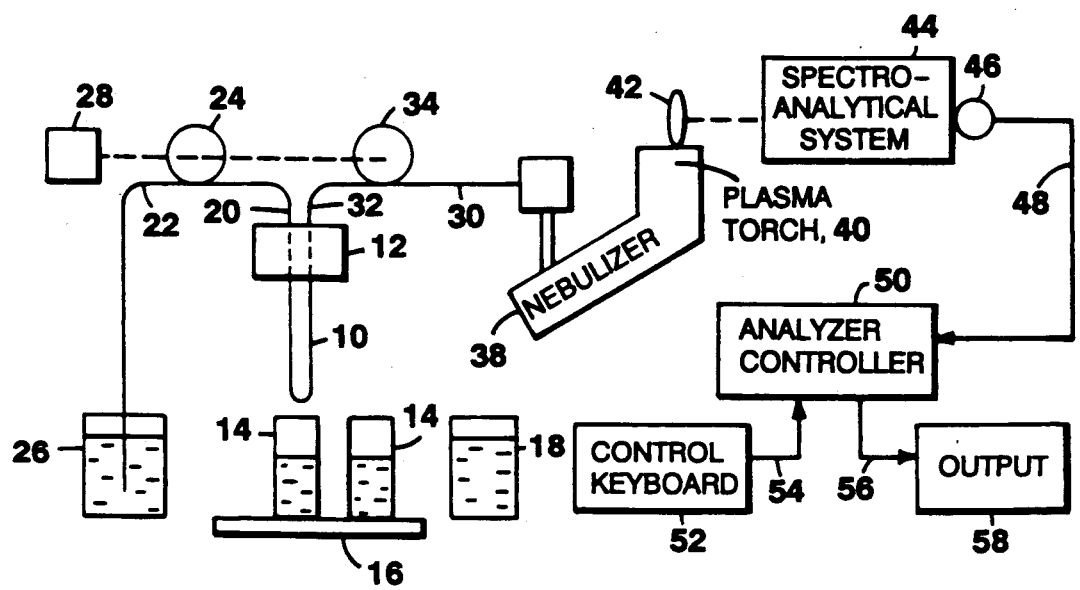
FIG. 1
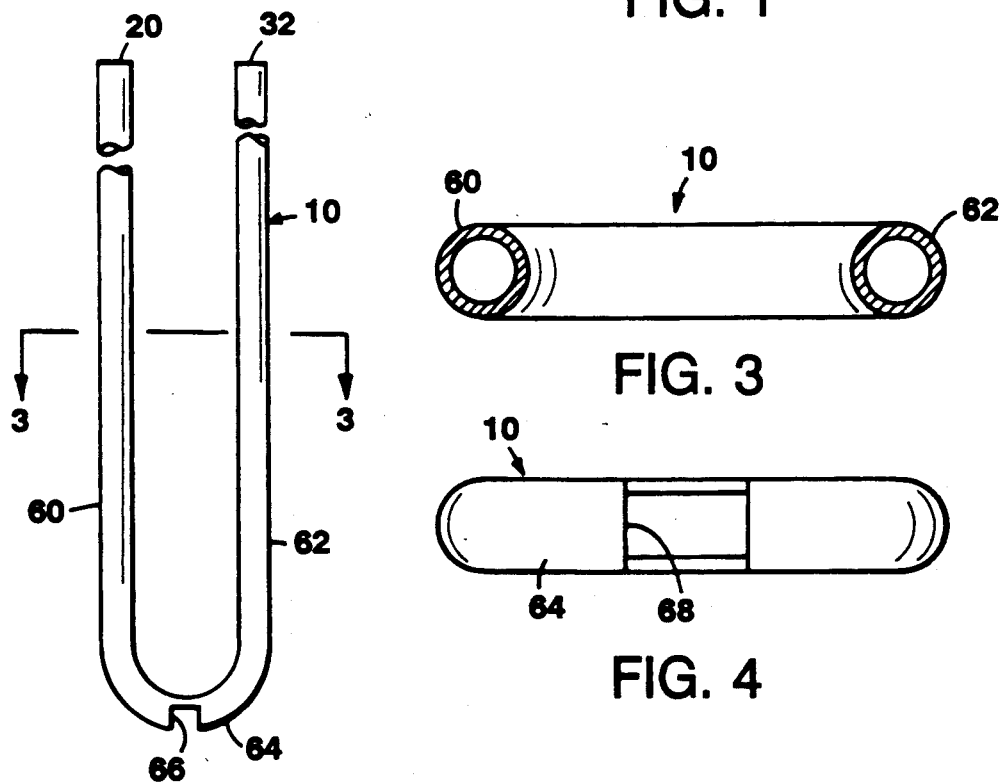
FIG. 2
FIG. 3
FIG. 4

SAMPLE PROCESSING

This invention relates to sample analysis apparatus, and more particularly to sample analysis apparatus particularly adapted for introducing a diluted viscous fluid into spectroanalysis apparatus or the like for trace element analysis.

Sample analysis is in wide spread use in industrial, clinical and medical environments. Frequently, samples to be analyzed are diluted with an appropriate diluent. Where the sample to be analyzed is a high viscosity material, such as an oil, a brine, a sludge or the like, such samples are difficult to aspirate, to dilute, and to clean from the sample processing system.

In accordance with one aspect of the invention, there is provided a sample processing system for use with analysis apparatus that includes tubular structure that defines a continuous elongated flow chamber. The tubular structure has an inlet port at one end, an outlet port at the other end, and a sample inlet port in communication with the continuous elongated flow chamber between the inlet and outlet ports. First flow structure flows diluent at a first rate through the inlet port for flow through the continuous elongated flow chamber, and second flow structure flows a liquid mixture from the continuous elongated flow chamber through the outlet port at a rate greater than the first rate. With the sample inlet port submerged in a sample to be analyzed, the sample is aspirated through the sample inlet port into the flowing diluent stream in the continuous elongated flow chamber for dilution and application of the diluted sample mixture to sample analysis apparatus for analysis.

In preferred embodiments, the tubular structure includes an elongated tube of uniform cross sectional area along its length, the tube is of U-shaped configuration with two parallel legs joined by a bight portion, the legs are spaced apart less than about two centimeters and the sample inlet port is disposed in the outer region of the bight portion. Preferably, the cross sectional area of the tube and the cross sectional area of the sample inlet port are each less than five square millimeters, and the effective flow area of the sample inlet port is greater than the effective cross sectional flow area of the elongated tube. In a particular embodiment, the sample probe tube has a volume of less than one milliliter and a cross sectional flow area of less than three square millimeters, and the sample tube is made of chemically inert material such as polytetrafluoroethylene or stainless steel. Each flow structure in that embodiment is a positive displacement peristaltic pump.

In accordance with another aspect of the invention, there is provided a spectroanalytical system that includes excitation apparatus for exciting sample material to spectroemissive levels, analysis apparatus in optically coupled relation to the sample excitation apparatus for generating data on elements in the sample that are excited to spectroemissive levels by the sample excitation apparatus, nebulizer apparatus coupled to the excitation apparatus for supplying a dispersion of sample material as an aerosol to the sample excitation apparatus, and tubular structure that defines a continuous elongated flow chamber. The tubular structure has an inlet port at one end, an outlet port at the other end, and a sample inlet port in communication with the continuous elongated flow chamber between the inlet and outlet ports. First flow structure flows diluent at a first rate through the inlet port for flow through the continuous elongated flow chamber, and second flow structure flows a liquid mixture from the continuous elongated flow chamber through the outlet port at a rate greater than the first rate. With the sample inlet port submerged in a sample to be analyzed, the sample is aspirated through the sample inlet port into the flowing diluent stream in the continuous elongated flow chamber for dilution and application of the diluted sample mixture to the nebulizer apparatus for supplying a dispersion of sample material as an aerosol to the sample excitation apparatus for excitation and analysis.

In preferred embodiments, the elongated tube has a volume of less than one milliliter and a length of at least twenty centimeters, and is of U-shaped configuration with two parallel legs and a bight portion in which the sample port is disposed. The sample inlet port has an area of about twice the cross sectional area of the elongated conduit and it is disposed at the outer end of the bight portion of the elongated conduit.

In a particular embodiment, each flow structure includes a positive displacement pump of the peristaltic type, the two pumps are driven at the same speed, and the inlet (diluent supply) tubing has a cross sectional area that is about two thirds the cross sectional area of the outlet (diluted sample) tubing. Where desired, a coil of tubing can be connected in line between the conduit outlet and the second positive displacement pump for additional mixing.

Other features and advantages of the invention will be seen as the following description of a particular embodiment progresses, in conjunction with the drawings, in which:

FIG. 1 is a diagram of a sample analysis system in accordance with the invention;

FIG. 2 is an elevational view of the U-shaped sample probe employed in the system shown in FIG. 1;

FIG. 3 is a sectional view of the sample probe taken along the line 3—3 of FIG. 2; and FIG. 4 is a bottom view of the sample probe shown in FIG. 2.

DESCRIPTION OF PARTICULAR EMBODIMENT

With reference to FIG. 1, the analyzer system includes sample probe 10 that is mounted on an autosampler mechanism diagrammatically indicated at 12 for insertion movement between a series of sixteen millimeter diameter sample containers 14 on table 16 and rinse station 18 of the ultrasonic cleaner type. Sample probe 10 has inlet port 20 that is connected by 1.65 millimeter inner diameter Viton tubing 22 through peristaltic pump 24 to diluent (kerosene) reservoir 26. 2.06 millimeter inner diameter Viton tubing 30 is connected from outlet port 32 of sample probe tube 10 through a second peristaltic pump 34 to nebulizer 38 which is coupled to induction coupled plasma torch 40. Pumps 24 and 34 are concurrently driven by adjustable speed motor 28. The output of torch 40 (diagrammatically indicated at 42) is monitored by spectroanalytical system 44 that includes radiation sensor 46 whose output is applied over line 48 to analyzer-controller 50 that receives inputs from control keyboard 52 over line 54 and provides outputs over lines 56 to one or more output devices 58 such as a display or a printer.

Further details of sample probe 10 may be had with reference to FIGS. 2–4. Probe tube 10 is of 15 gauge stainless steel tubing that has an outer diameter of about 1.8 millimeters, an inner diameter of about 1.3 millimeters and a wall thickness of about 0.2 millimeter. Tube 10 has parallel legs 60, 62, that are each about eighteen centimeters in length and that are spaced about one centimeter apart, and a bight portion 64 of smoothly curved, semicircular configuration. Formed in the lower portion of bight 64 is rectangular sample inlet port 66 that has a length of about 2.2 millimeter and a width of about 1.3 millimeters so that the cross sectional area of port 66 is about twice the cross sectional area of the flow passage in leg portions 60 and 62. Probe tube 10 has a volume of about one-half milliliter.

In standby, the inlet port 66 of sample probe 10 is submerged in the cleaning liquid (e.g., kerosene) in reservoir 18. When pump motor 28 is turned on, pump 24 draws diluent from reservoir 26 into sample probe 10 and pump 34 draws the liquid from probe 10 at a faster rate, creating reduced pressure at port 66 to aspirate cleaning liquid into sample probe 10 for mixing with the diluent and flow of the mixture by pump 34 over line 30 through nebulizer 38 to waste.

When a sample is to be analyzed, motor 28 is driven at a relatively high speed (120-200 RPM) and the probe tube 10 is moved by autosampler mechanism 12 and submerged in a sample in a container 14 on the sample table 16. The sample is aspirated through port 66 into the flow of diluent from leg 60 and through leg 62 and tubing 30 for mixing with the diluent and flow by pump 34 into nebulizer 38. Dispersion of the diluted sample as an aerosol occurs in nebulizer 38 and the resulting mixture in nebulized form is flowed to the ICP torch 40 where the sample is excited to spectroemissive levels for monitoring by spectroanalyzer 4 and application of signals to analyzer-controller 50 and generation of output signals to output devices 58.

While a particular embodiment of the invention has been shown and described, various modifications thereof will be apparent to those skilled in the art, and therefore, it is not intended that the invention be limited to the disclosed embodiment, or to details thereof, and departures may be made therefrom within the spirit and scope of the invention.

What is claimed is:

1. A sample processing system for use with analysis apparatus comprising tubular structure defining a continuous elongated flow chamber, said tubular structure having an inlet port at one end of said elongated flow chamber, an outlet port at the other end of said elongated flow chamber, and a sample inlet port in said tubular structure in communication with said continuous elongated flow chamber between said inlet and outlet ports,
   first flow structure for flowing diluent through said inlet port at a first rate for flow through said continuous elongated flow chamber, and
   second flow structure for flowing a liquid mixture from said continuous elongated flow chamber through said outlet port at a rate greater than said first rate while said sample inlet port is submerged in a sample to be analyzed to aspirate that sample to be analyzed through said sample inlet port into the flowing diluent stream in said continuous elongated flow chamber for dilution and application of the diluted sample mixture to sample analysis apparatus for analysis.

2. The system of claim 1 wherein said tubular structure includes an elongated tube of uniform cross sectional area along its length, said tube being of U-shaped configuration with two parallel legs joined by a bight portion, said legs being spaced apart less than about two centimeters and said sample inlet port being disposed in the outer region of said bight portion, the cross sectional area of said tube being less than five square millimeters and the cross sectional area of said sample inlet port being less than five square millimeters.

3. The system of claim 2 wherein the effective flow area of said inlet port is greater than the effective cross sectional flow area of said elongated tube.

4. The system of claim 3 wherein said elongated tube has a volume of less than one milliliter and a cross sectional flow area of less than three square millimeters.

5. The system of claim 4 wherein said elongated tube is made of chemically inert material.

6. The system of claim 5 wherein each said flow structure includes a positive displacement pump.

7. The system of claim 1 wherein the effective flow area of said inlet port is greater than the effective cross sectional flow area of said tubular structure.

8. The system of claim 1 wherein said elongated flow chamber has a volume of less than one milliliter and a cross sectional flow area of less than three square millimeters.

9. The system of claim 1 wherein said tubular structure is made of chemically inert material.

10. The system of claim 1 wherein each said flow structure includes a positive displacement pump.

11. A spectroanalytical system comprising
    excitation apparatus for exciting sample material to spectroemissive levels,
    analysis apparatus in optically coupled relation to said sample excitation apparatus for generating data on elements in said sample that are excited to spectroemissive levels by said sample excitation apparatus,
    nebulizer apparatus coupled to said excitation apparatus for supplying a dispersion of sample material as an aerosol to said sample excitation apparatus,
    tubular structure defining a continuous elongated flow chamber, said tubular structure having an inlet port at one end of said elongated flow chamber, an outlet port at the other end of said elongated flow chamber, and a sample inlet port in said tubular structure in communication with said continuous elongated flow chamber between said inlet and outlet ports,
    first flow structure including inlet tubing coupled to said inlet port for flowing diluent through said inlet port at a first rate for flow through said continuous elongated flow chamber, and
    second flow structure including outlet tubing coupled to said outlet port for flowing a liquid mixture from said continuous elongated flow chamber through said outlet port at a rate greater than said first rate while said sample inlet port is submerged in a sample to be analyzed to aspirate that sample to be analyzed through said sample inlet port into the flowing diluent stream in said continuous elongated flow chamber for dilution and application of the diluted sample mixture to said nebulizer apparatus.

12. The system of claim 11 wherein said continuous elongated flow chamber has a volume of less than one milliliter and a length of at least twenty centimeters.

13. The system of claim 11 wherein said continuous elongated flow chamber is of U-shaped configuration with two parallel legs and a bight portion in which said sample inlet port is disposed.

14. The system of claim 13 wherein said sample inlet port has an area of about twice the cross sectional area of the elongated flow chamber and is disposed at the outer end of said bight portion.

15. The system of claim 11 wherein each said flow structure includes a positive displacement pump of the peristaltic type, said system includes operating structure for driving said pumps at the same speed, and said inlet tubing has a cross sectional area that is less than the cross sectional area of said outlet tubing.

16. The system of claim 11 wherein said continuous elongated flow chamber is a tube of U-shaped configuration with two parallel legs and a bight portion, and has a length of at least twenty centimeters and a volume of less than one milliliter, and said sample inlet port has an area of about twice the cross-sectional flow area of said tube and is disposed at the outer surface of said bight portion.

17. The system of claim 16 wherein each said flow structure includes a positive displacement pump of the peristaltic type, said system includes operating structure for concurrently driving said pumps at the same speed, and said inlet tubing has a cross sectional area that is about two thirds the cross sectional area of said outlet tubing.

* * * * *